US011369254B2

(12) United States Patent
Sato et al.

(10) Patent No.: US 11,369,254 B2
(45) Date of Patent: Jun. 28, 2022

(54) ENDOSCOPE AND IMAGE CAPTURING UNIT PROVIDED THEREIN

(71) Applicants: NIREC CORPORATION, Kochi (JP); NATIONAL UNIVERSITY CORPORATION KOCHI UNIVERSITY, Kochi (JP)

(72) Inventors: Takayuki Sato, Kochi (JP); Haruyasu Katahira, Kanagawa (JP); Tetsuo Sumida, Kochi (JP); Shigehiro Kanayama, Saitama (JP)

(73) Assignees: NIREC CORPORATION, Kochi (JP); NATIONAL UNIVERSITY CORPORATION KOCHI UNIVERSITY, Kochi (JP)

(*) Notice: Subject to any disclaimer, the term of this patent is extended or adjusted under 35 U.S.C. 154(b) by 0 days.

(21) Appl. No.: 17/493,014

(22) Filed: Oct. 4, 2021

(65) Prior Publication Data
US 2022/0104691 A1 Apr. 7, 2022

(30) Foreign Application Priority Data
Oct. 5, 2020 (JP) .............................. JP2020-168514

(51) Int. Cl.
A61B 1/00 (2006.01)
A61B 1/05 (2006.01)
(Continued)

(52) U.S. Cl.
CPC .......... A61B 1/00096 (2013.01); A61B 1/051 (2013.01); G02B 23/243 (2013.01);
(Continued)

(58) Field of Classification Search
CPC .. A61B 1/00096; A61B 1/051; G02B 23/243; G02B 23/2484; H04N 5/2254; H04N 5/238; H04N 2005/2255
See application file for complete search history.

(56) References Cited

U.S. PATENT DOCUMENTS 5,910,816 A * 6/1999 Fontenot .............. A61B 5/0059
348/65
8,208,015 B2 * 6/2012 Unsai ..................... A61B 1/051
348/72

(Continued)

FOREIGN PATENT DOCUMENTS

JP 2002-102144 A 4/2002
JP 2005-514147 A 5/2005
(Continued)

OTHER PUBLICATIONS

Dec. 8, 2020, Japanese Office Action issued for related JP application No. 2020-168514.

Primary Examiner — Boubacar Abdou Tchoussou
(74) Attorney, Agent, or Firm — Paratus Law Group, PLLC

(57) ABSTRACT

An endoscope includes a scope and an image capturing unit accommodated inside the scope. The image capturing unit includes: first and second prisms; a reflection film provided between oblique faces of the first and second prisms; a first trimming filter on which visible light transmitted through the first prism is incident on the first trimming filter via the reflection film; a first image sensor facing the first trimming filter; a second trimming filter on which near-infrared light transmitted through the second prism being incident on the second trimming filter via the reflection film; and a second image sensor facing the second trimming filter. The first (Continued)

prism is fixed to the second prism, the first trimming filter is fixed to the first prism, and the second trimming filter is fixed to the second prism.

15 Claims, 10 Drawing Sheets

(51) Int. Cl.
  *H04N 5/238* (2006.01)
  *G02B 23/24* (2006.01)
  *H04N 5/225* (2006.01)
(52) U.S. Cl.
  CPC ....... *G02B 23/2484* (2013.01); *H04N 5/2254* (2013.01); *H04N 5/238* (2013.01); *H04N 2005/2255* (2013.01)

(56) References Cited

U.S. PATENT DOCUMENTS

| | | | |
|---|---|---|---|
| 8,602,972 B2* | 12/2013 | Unsai | A61B 1/00096 600/110 |
| 10,694,117 B2* | 6/2020 | Frangioni | A61B 1/3132 |
| 10,902,572 B1* | 1/2021 | Kennedy | G02B 27/126 |
| 2003/0135092 A1 | 7/2003 | Cline et al. | |
| 2005/0143627 A1 | 6/2005 | Cline et al. | |
| 2005/0154319 A1 | 7/2005 | Cline et al. | |
| 2006/0241496 A1 | 10/2006 | Fengler et al. | |
| 2007/0015963 A1 | 1/2007 | Fengler et al. | |
| 2009/0236541 A1* | 9/2009 | Lomnes | A61B 1/05 250/458.1 |
| 2012/0002956 A1 | 1/2012 | McDowall | |
| 2012/0016230 A1 | 1/2012 | Kishima et al. | |
| 2013/0027533 A1 | 1/2013 | McDowell | |
| 2014/0194687 A1 | 7/2014 | Fengler et al. | |
| 2016/0270640 A1 | 9/2016 | Fengler et al. | |
| 2016/0317003 A1 | 11/2016 | Ogata et al. | |
| 2019/0170647 A1 | 6/2019 | Ikenaga et al. | |
| 2019/0180865 A1 | 6/2019 | Kashima et al. | |
| 2019/0247126 A1 | 8/2019 | Ikehara | |
| 2019/0298151 A1* | 10/2019 | Frangioni | A61B 1/00186 |
| 2019/0357757 A1 | 11/2019 | Fengler et al. | |
| 2020/0243185 A1 | 7/2020 | Kashima et al. | |
| 2021/0298566 A1* | 9/2021 | Levy | A61B 1/0019 |

FOREIGN PATENT DOCUMENTS

| | | |
|---|---|---|
| JP | 2005-176940 A | 7/2005 |
| JP | 2010-082041 A | 4/2010 |
| JP | 2011-101763 A | 5/2011 |
| JP | 2011-211553 A | 10/2011 |
| JP | 2012-023492 A | 2/2012 |
| JP | 2016-209143 A | 12/2016 |
| JP | 2016-209629 A | 12/2016 |
| JP | 2017-221486 A | 12/2017 |
| JP | 2018-027272 A | 2/2018 |
| JP | 2018-175762 A | 11/2018 |
| JP | 2019-000339 A | 1/2019 |
| JP | 2019-063217 A | 4/2019 |
| JP | 2019-136269 A | 8/2019 |
| JP | 2020-062437 A | 4/2020 |

* cited by examiner

ENDOSCOPE AND IMAGE CAPTURING UNIT PROVIDED THEREIN

CROSS-REFERENCE TO RELATED APPLICATIONS

This application is based on and claims the benefit of priority of Japanese Patent Application No. 2020-168514 filed on Oct. 5, 2020, the entire contents of which are incorporated herein by reference.

FIELD

The present disclosure relates to an endoscope and an image capturing unit provided in the endoscope.

BACKGROUND

JP-A-2016-209143 discloses an endoscope in which a single image sensor including an RGB color filter and an infrared light (IR) filter is disposed in a vicinity of a tip end of a scope. In the endoscope of JP-A-2016-209143, biological tissue of a patient is alternately irradiated with visible light and excitation light, and thus visible light image data and near-infrared light image data is alternately acquired on a time axis by the single image sensor. In this regard, the endoscope of JP-A-2016-209143 has a problem that the visible light image data and the near-infrared light image data cannot be acquired at the same timing. Further, four types of pixels including a red pixel, a green pixel, a blue pixel, and an IR pixel, are provided in the single image sensor. Therefore, there is a problem that noise is likely to occur in an infrared light image signal output from each IR pixel of the image sensor, and image quality of the near-infrared light image data to be finally generated may be deteriorated.

Meanwhile, JP-A-2019-000339 discloses an endoscope in which a four-color separation prism and four image sensors are disposed in a camera head. In the endoscope of JP-A-2019-000339, light emitted from a relay lens is separated into four light components of red light, green light, blue light, and near-infrared light by the four-color separation prism, and then each of the four light components is received by a corresponding image sensor among the four image sensors. The endoscope of JP-A-2019-000339 can acquire visible light image data and near-infrared light image data at the same time. On the other hand, since the four image sensors are disposed at positions away from a tip end of a scope (optical tube), light intensity (an amount of light) of the visible light and the near-infrared light (particularly, the near-infrared light) decreases during a period before the visible light and the near-infrared light associated with biological tissue of a patient reach the four image sensors. As a result, there is a problem that the image quality of the visible light image data and the near-infrared light image data is deteriorated. Further, since an entire size of the four-color separation prism is large, it is necessary to dispose the four-color separation prism in, for example, a camera head. For this reason, in order to guide the visible light and the near-infrared light reflected by the biological tissue of the patient from the tip end of the scope to the four-color separation prism, it is necessary to provide expensive optical components such as a relay lens in the endoscope, and a manufacturing cost of the entire endoscope may increase.

SUMMARY

From the above viewpoint, an object of the present disclosure is to provide an endoscope capable of improving the image quality of visible light image data and near-infrared light image data indicating biological tissue of a patient while reducing a manufacturing cost, and an image capturing unit provided in the endoscope.

An aspect of the present disclosure may provide an endoscope including: a scope to be inserted into a body of a patient; and an image capturing unit accommodated inside the scope and configured to receive light associated with biological tissue of the patient so as to capture an image of the biological tissue. The image capturing unit includes: a first prism; a second prism facing the first prism; a reflection film provided between an oblique face of the first prism and an oblique face of the second prism and configured to separate the light associated with the biological tissue into visible light and near-infrared light; a first trimming filter configured to transmit light in a visible region and to shield light in a near-infrared region, the visible light transmitted through the first prism being incident on the first trimming filter via the reflection film; a first image sensor facing the first trimming filter so as to receive the visible light transmitted through the first trimming filter, and configured to convert the received visible light into an electric signal; a second trimming filter configured to transmit light in the near-infrared region and to shield light in the visible region, the near-infrared light transmitted through the second prism being incident on the second trimming filter via the reflection film; and a second image sensor facing the second trimming filter so as to receive the near-infrared light transmitted through the second trimming filter, and configured to convert the received near-infrared light into an electric signal. The first prism is fixed to the second prism, the first trimming filter is fixed to the first prism, and the second trimming filter is fixed to the second prism.

According to the above configuration, the first prism and the second prism are fixed to each other. Further, the first trimming filter is fixed to the first prism, and the second trimming filter is fixed to the second prism. With such a configuration, a size of the entire image capturing unit can be reduced, and the image capturing unit can be accommodated inside the scope. Since the image capturing unit is accommodated inside the scope, the visible light and the near-infrared light associated with the biological tissue of the patient is efficiently received by the first image sensor and the second image sensor, respectively. As described above, since the electric signal (visible light image signal) indicating the biological tissue is acquired by the first image sensor without decreasing a SN ratio (signal-to-noise ratio), image quality of the visible light image data indicating the biological tissue is improved. Further, since the electrical signal (near-infrared light image signal) indicating the biological tissue is acquired by the second image sensor without decreasing a SN ratio, image quality of the near-infrared image data indicating the biological tissue is improved. Since the visible light image signal and the near-infrared light image signal are acquired at the same timing, a time axis of each frame of the visible light image data and a time axis of each frame of the near-infrared light image data match with each other. Thus, since the time axis of the frame of the visible light image data and the time axis of the frame of the near-infrared light image data match, accuracy of the composite image data generated by synthesizing the visible light image data and the near-infrared light image data is improved. Further, since the image capturing unit is accommodated inside the scope, there is no need to provide, on the scope, an expensive relay lens or the like for guiding the visible light and the near-infrared light from the biological tissue of the patient to the image capturing unit, so that a manufacturing cost of the entire endoscope can be reduced. Therefore, it is possible to provide an endoscope capable of improving the image quality of the visible light image data and the near-infrared light image data indicating the biological tissue of the patient while reducing the manufacturing cost.

In the endoscope, the first image sensor may be fixed to the first trimming filter, and the second image sensor may be fixed to the second trimming filter.

According to the above configuration, the size of the entire image capturing unit can be reduced, and the image capturing unit can be accommodated inside the scope. In this regard, for example, the image capturing unit can be accommodated inside a scope having a small inner diameter.

In the endoscope, the image capturing unit may be disposed in a vicinity of a tip end surface of the endoscope facing the biological tissue.

According to the above configuration, since the image capturing unit is disposed in the vicinity of the tip end surface of the endoscope facing the biological tissue, the first image sensor and the second image sensor can efficiently receive the visible light and the near-infrared light associated with the biological tissue of the patient. As a result, the image quality of the visible light image data and the near-infrared light image data acquired through the endoscope is improved.

In the endoscope, the image capturing unit may further include: an infrared light shielding film provided between the first trimming filter and the first image sensor and configured to transmit light in the visible region and to shield light in the near-infrared region; and a visible light shielding film provided between the second trimming filter and the second image sensor and configured to transmit light in the near-infrared region and to shield light in the visible region. The infrared light shielding film and the visible light shielding film may be configured to shield excitation light emitted to the biological tissue and included in a wavelength band having a center wavelength of 700 nm to 800 nm.

According to the above configuration, since the excitation light in the wavelength band having a center wavelength of 700 nm to 800 nm emitted to the biological tissue is shield by the infrared light shielding film and the visible light shielding film, a situation in which the excitation light adversely affects the image quality of the visible light image data and the near-infrared light image data can be suitably prevented.

In the endoscope, the image capturing unit may further include: a lens unit fixed to the first prism so as to guide the light associated with the biological tissue toward the first prism.

According to the above configuration, the visible light and the near-infrared light associated with the biological tissue can be efficiently incident on the first prism due to the lens unit, and an appropriate angle of view of the image capturing unit can be secured. Further, since no gap is provided between the lens unit and the first prism, dust or the like can be suitably prevented from entering the gap, and a burden required for maintenance of the endoscope can be reduced.

In the endoscope, a distance between a tip end of the lens unit and a tip end surface of the endoscope facing the biological tissue may be in a range of 0.5 mm to 5 mm.

According to the above configuration, since the distance between the tip end of the lens unit and the tip end surface of the endoscope facing the biological tissue is in the range of 0.5 mm to 5 mm, the first image sensor and the second image sensor can efficiently receive the visible light and the near-infrared light reflected by the biological tissue of the patient. Further, an appropriate angle of view of the image capturing unit can be secured.

The endoscope may further include a first support member configured to support the lens unit, the first prism, and the second prism, and accommodated inside the scope. The first support member may be fixed to the lens unit, the first prism, and the second prism.

According to the above configuration, since the lens unit, the first prism, and the second prism are supported and fixed by the first support member, strength of the entire image capturing unit can be improved by the first support member.

The endoscope may further include a second support member fixed to the first support member and the scope and accommodated inside the scope.

According to the above configuration, the first support member fixed to the image capturing unit is fixed to the scope via the second support member. In this way, the image capturing unit can be reliably fixed to the scope by the first support member and the second support member.

In the endoscope, the first image sensor may include a CMOS image sensor configured to generate, based on the visible light forming an inverted image of the biological tissue, a visible light image signal indicating a normal image of the biological tissue.

According to the above configuration, since the first image sensor is a CMOS image sensor configured to generate the visible light image signal indicating the normal image of the biological tissue, the visible light image data and the near-infrared light image data can be acquired at the same timing. Specifically, in a case where the first image sensor is a CCD image sensor, it is necessary to separately perform, on an image processing circuit side, image inversion processing for generating the visible light image data indicating the normal image of the biological tissue based on the visible light image signal indicating the inverted image of the biological tissue. For this reason, a situation may occur in which a generation timing of the visible light image data is later than a generation timing of the near-infrared light image data, and it is difficult to acquire the visible light image data and the near-infrared light image data at the same timing on the image processing circuit side. Meanwhile, in a case where the first image sensor is a CMOS image sensor, since there is no need to perform the image inversion processing on the image processing circuit side, the visible light image data and the near-infrared light image data can be acquired at the same timing on the image processing circuit side.

In the endoscope, the first image sensor and the second image sensor may have a same configuration.

According to the above configuration, since there is no need to prepare different types of image sensors for the first image sensor and the second image sensor, the manufacturing cost of the endoscope can be reduced. For example, a CMOS image sensor including a Bayer pattern color filter array can be applied to both the first image sensor and the second image sensor.

In the endoscope, an imaging surface of the first image sensor and an imaging surface of the second image sensor may be perpendicular to each other.

According to the above configuration, since the imaging surface of the first image sensor and the imaging surface of the second image sensor are perpendicular to each other, the size of the entire image capturing unit can be reduced, and the image capturing unit can be successfully accommodated inside the scope.

In the endoscope, a visible light channel formed by a combination of the reflection film, the first trimming filter, and the infrared light shielding film may have spectral characteristics such that transmittance of light in a wavelength band of 720 nm to 1050 nm is 0.1% or less, and a near-infrared light channel formed by a combination of the reflection film, the second trimming filter, and the visible light shielding film may have spectral characteristics such that transmittance of light in a wavelength band of 400 nm to 798 nm is 0.5% or less.

According to the above configuration, the visible light channel formed by the combination of the reflection film, the first trimming filter, and the infrared light shielding film has spectral characteristics such that the transmittance of light in a wavelength band of 720 nm to 1050 nm is 0.1% or less. Therefore, a situation in which the excitation light in a wavelength band of 700 nm to 800 nm and the near-infrared light both being emitted to the biological tissue adversely affects the image quality of the visible light image data can be suitably prevented. Further, the near-infrared light channel formed by the combination of the reflection film, the second trimming filter, and the visible light shielding film has spectral characteristics such that the transmittance of light in a wavelength band of 400 nm to 798 nm is 0.5% or less. Therefore, a situation in which the excitation light in a wavelength band of 700 nm to 800 nm and the visible light both being emitted to the biological tissue adversely affects the image quality of the near-infrared light image data can be suitably prevented.

An aspect of the present disclosure may provide an image capturing unit accommodated inside a scope of an endoscope and configured to receive light associated with biological tissue of a patient so as to capture an image of the biological tissue. The image capturing unit includes: a first prism; a second prism facing the first prism; a reflection film provided between an oblique face of the first prism and an oblique face of the second prism and configured to separate the light associated with biological tissue into visible light and near-infrared light; a first trimming filter configured to transmit light in a visible region and to shield light in a near-infrared region, the visible light transmitted through the first prism being incident on the first trimming filter via the reflection film, a first image sensor facing the first trimming filter so as to receive the visible light transmitted through the first trimming filter, and configured to convert the received visible light into an electric signal; a second trimming filter configured to transmit light in the near-infrared region and to shield light in the visible region, the near-infrared light transmitted through the second prism being incident on the second trimming filter via the reflection film; and a second image sensor facing the second trimming filter so as to receive the near-infrared light transmitted through the second trimming filter, and configured to convert the received near-infrared light into an electric signal. The first prism is fixed to the second prism, the first trimming filter is fixed to the first prism, and the second trimming filter is fixed to the second prism.

According to the present disclosure, it is possible to provide an endoscope capable of improving the image quality of the visible light image data and the near-infrared light image data indicating the biological tissue of the patient while reducing the manufacturing cost, and an image capturing unit provided in the endoscope.

DETAILED DESCRIPTION

Figure 1:
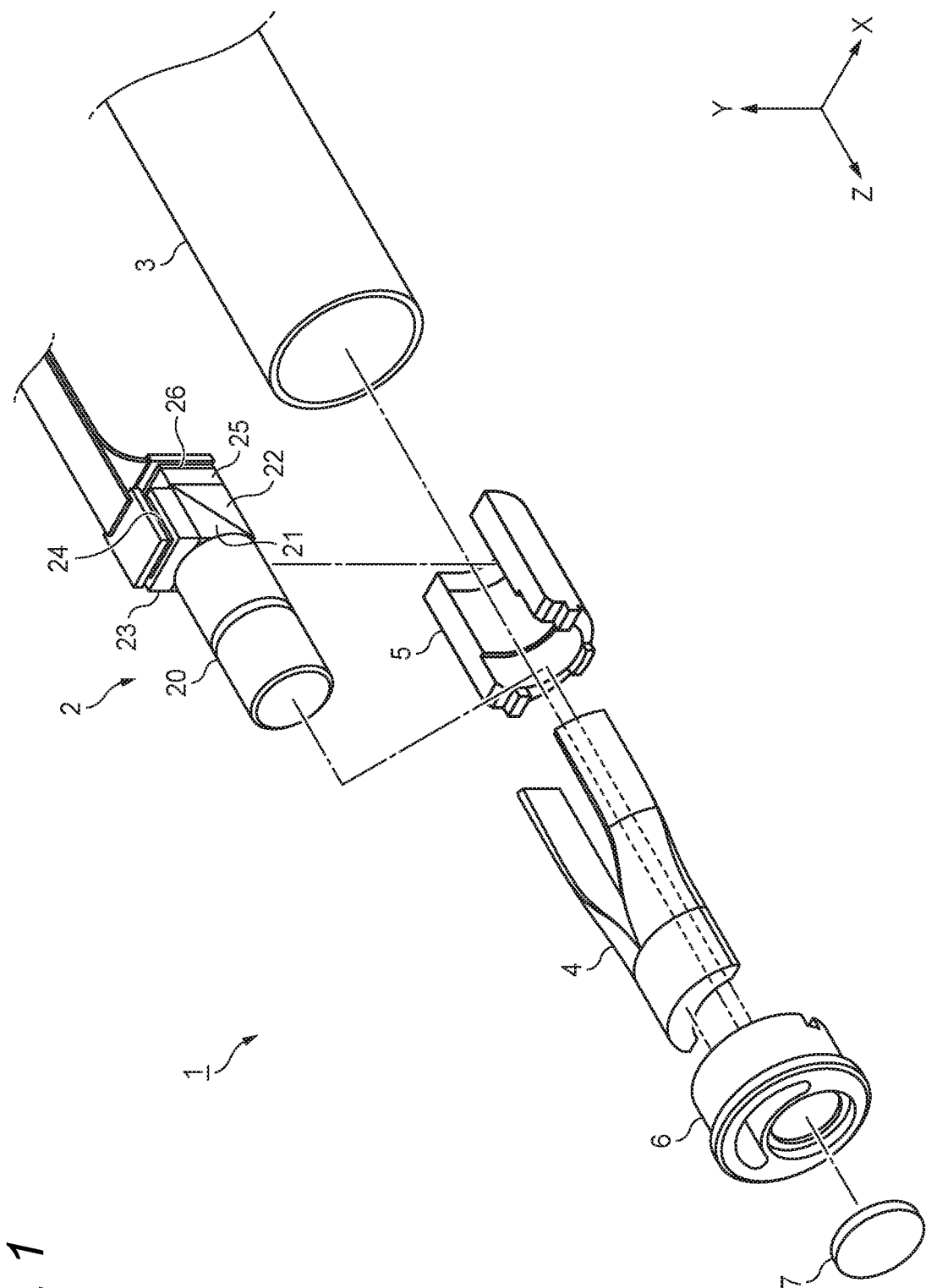
FIG. 1 is an exploded perspective view showing an endoscope according to the present embodiment.

Hereinafter, an endoscope 1 according to an embodiment (hereinafter, simply referred to as "the present embodiment") of the present disclosure will be described with reference to the drawings. Dimensions of each member shown in the drawings may be different from actual dimensions of the each member for convenience of description.

In the description of the present embodiment, for convenience of description, X-axis, Y-axis, and Z-axis directions of the endoscope 1 may be referred to as appropriate. These directions are relative directions set for the endoscope 1 shown in FIG. 1. It is defined that one of an X axis, a Y axis, and a Z axis is orthogonal to the remaining two axes. The Z axis corresponds to an extending direction of a scope 3 of the endoscope 1.

Figure 2:
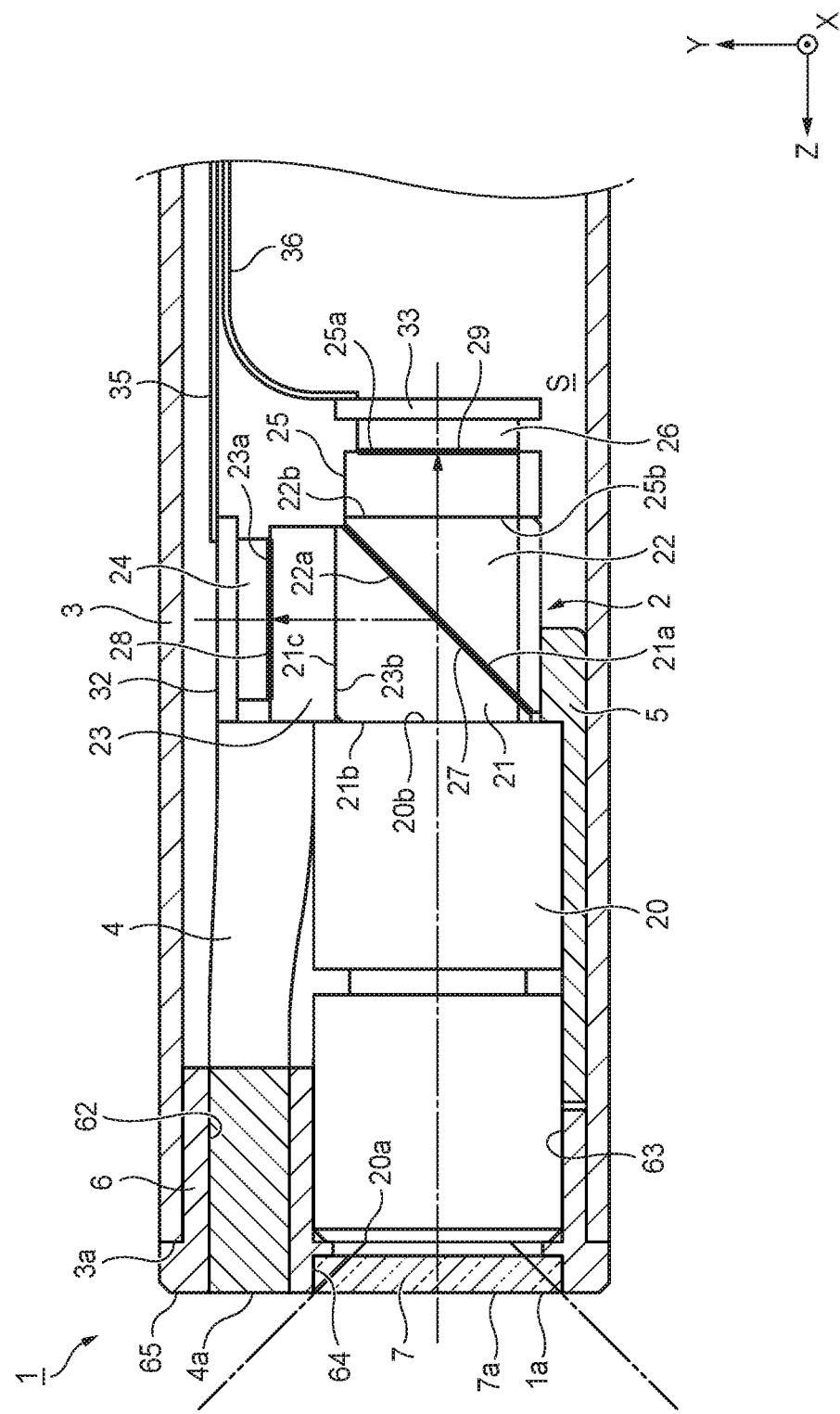
FIG. 2 is a cross-sectional view showing the endoscope according to the present embodiment.

First, a configuration of the endoscope 1 according to the present embodiment will be described below with reference to FIG. 1 and FIG. 2. FIG. 1 is an exploded perspective view showing the endoscope 1 according to the present embodiment. FIG. 2 is a cross-sectional view showing the endoscope 1 in a state in which an image capturing unit 2 is accommodated inside the scope 3.

As shown in FIG. 1 and FIG. 2, the endoscope 1 includes the scope 3, the image capturing unit 2, a light guide 4, a first support member 5, a second support member 6, and a lens cover 7. By inserting the endoscope 1 into a body of a patient, a health care worker can observe biological tissue such as an internal body of the patient in real time. The endoscope 1 may be, for example, a rigid endoscope used under laparoscopic surgery. The endoscope 1 is not limited to the rigid endoscope.

Both visible light image data and near-infrared light image data of the biological tissue of the patient can be simultaneously acquired through the endoscope 1. In this regard, under laparoscopic surgery, a fluorescent contrast agent that emits near-infrared light, such as indocyanine green (ICG), is used. When the ICG is irradiated with excitation light (laser light), the ICG emits near-infrared light. A center wavelength λ of the laser light as the excitation light is, for example, in a range of 700 nm to 800 nm, more specifically, in a range of 785 nm to 795 nm. After injecting the ICG into vein of the patient, the health care worker can visually specify an affected part where the ICG stays by visually recognizing the near-infrared light image data acquired through the endoscope 1. In this way, a health care worker such as a surgeon can perform a surgical treatment (such as resection of an affected part) on the affected part specified by the ICG.

The scope 3 is a portion of the endoscope 1 to be inserted into the body of the patient. The scope 3 is configured as, for example, a rigid tube having a space S. An outer diameter of the scope 3 is, for example, about 10 mm, and an inner diameter of the scope 3 is, for example, about 9 mm. The image capturing unit 2 is configured to receive visible light and near-infrared light associated with biological tissue of a patient so as to capture an image of the biological tissue. Specifically, the image capturing unit 2 is configured to receive the visible light reflected by the biological tissue of the patient and the near-infrared light emitted from the fluorescent contrast agent (ICG or the like) staying in the biological tissue so as to capture the image of the biological tissue. In the present embodiment, the image capturing unit 2 is accommodated inside the space S of the scope 3. In this regard, the image capturing unit 2 is downsized to such an extent that the image capturing unit 2 can be accommodated inside the scope 3 having an inner diameter of about 9 mm. Further, the image capturing unit 2 is disposed in a vicinity of a tip end 3a (see FIG. 2) of the scope 3. The tip end 3a of the scope 3 faces the biological tissue of the patient in a state where the endoscope 1 is inserted into the body of the patient. A specific configuration of the image capturing unit 2 will be described later.

The light guide 4 is configured to guide visible light emitted from a visible light source (not shown) and excitation light emitted from an excitation light source (not shown) toward the biological tissue of the patient. The light guide 4 includes many optical fibers through which the visible light and the excitation light propagates. In FIG. 1, only a part of the light guide 4 is illustrated from the viewpoint of simplification of illustration, but the light guide 4 is accommodated inside the space S of the scope 3 and extends to the visible light source and the excitation light source along the Z-axis direction. The visible light emitted from the light guide 4 is reflected by the biological tissue and then received by the image capturing unit 2. Further, the excitation light emitted from the light guide 4 is emitted to the fluorescent contrast agent such as the ICG staying in the biological tissue. Thereafter, the near-infrared light (fluorescence) emitted from the fluorescent contrast agent through irradiation with excitation light is received by the image capturing unit 2.

As shown in FIG. 2, the first support member 5 is accommodated inside the space S of the scope 3, and is configured to support the image capturing unit 2. In particular, the first support member 5 is fixed to the image capturing unit 2 by an adhesive. More specifically, the first support member 5 is configured to support a lens unit 20, a first prism 21, and a second prism 22 that are provided in the image capturing unit 2, and is fixed to the lens unit 20, the first prism 21, and the second prism 22 by an adhesive. In this way, strength of the entire image capturing unit 2 can be improved by the first support member 5.

The second support member 6 is accommodated inside the space S of the scope 3, and is fixed to the first support member 5 and the scope 3 by an adhesive. The second support member 6 includes an insertion hole 62 into which the light guide 4 is inserted, an insertion hole 63 into which the lens unit 20 is inserted, and an insertion hole 64 into which the lens cover 7 is inserted. In a state where the light guide 4 is inserted into the insertion hole 62, the light guide 4 is supported by the second support member 6. The insertion hole 63 and the insertion hole 64 are in communication with each other. In a state where the lens cover 7 is inserted into the insertion hole 64, the lens cover 7 is fixed and supported by the second support member 6. A front surface 65 of the second support member 6, a front surface 7a of the lens cover 7, and an end surface 4a of the light guide 4 form a tip end surface 1a of the endoscope 1 facing the biological tissue.

As described above, since the first support member 5 is fixed to the image capturing unit 2 and the second support member 6 is fixed to the first support member 5 and the scope 3, the image capturing unit 2 can be reliably fixed to the scope 3 by the first support member 5 and the second support member 6.

(Specific Configuration of Image Capturing Unit 2)

Next, a specific configuration of the image capturing unit 2 will be described below with reference to FIG. 2. As shown in FIG. 2, the image capturing unit 2 includes the lens unit 20, the first prism 21, the second prism 22, and a visible light reflection film 27 (an example of a reflection film). The image capturing unit 2 further includes a first trimming filter 23, an infrared light shielding film 28, a first image sensor 24, and a first circuit board 32. The image capturing unit 2 further includes a second trimming filter 25, a visible light shielding film 29, a second image sensor 26, and a second circuit board 33.

The lens unit 20 is configured to guide the visible light and the near-infrared light from the biological tissue toward the first prism 21. In order to widen an angle of image (angle of view) of the image capturing unit 2 and more efficiently take in the visible light and the near-infrared light from the biological tissue, it is preferable to dispose the lens unit 20 in a vicinity of the tip end 3a of the scope 3 or in a vicinity of the tip end surface 1a of the endoscope 1. In the present embodiment, a distance between an incident surface 20a of the lens unit 20, which is a tip end of the lens unit 20, and the tip end surface 1a of the endoscope 1 in the Z-axis direction is in a range of 0.5 mm to 5 mm. Preferably, the distance between the incident surface 20a and the tip end surface 1a in the Z-axis direction is in a range of 0.5 mm to 2 mm. More preferably, the distance between the incident surface 20a and the tip end surface 1a in the Z-axis direction is in a range of 0.5 mm to 1 mm.

The lens unit 20 and the first prism 21 are fixed to each other via the first support member 5. In this regard, an emission surface 20b of the lens unit 20 and an incident surface 21b of the first prism 21 are in contact with each other, and there is no gap between the lens unit 20 and the first prism 21. Therefore, dust or the like can be suitably prevented from entering the gap, and a burden required for maintenance of the endoscope 1 can be reduced.

The first prism 21 and the second prism 22 are configured as right-angle prisms. The first prism 21 and the second prism 22 are formed of, for example, a transparent glass material or a transparent plastic material. The first prism 21 and the second prism 22 face each other and are fixed to each other by an adhesive. In particular, the first prism 21 and the second prism 22 are fixed to each other in a state where an oblique face 21a of the first prism 21 and an oblique face 22a of the second prism 22 face each other. Thus, since a shape of the first prism 21 and the second prism 22 fixed to each other is a rectangular parallelepiped shape, a size of the entire image capturing unit 2 can be reduced and the image capturing unit 2 can be accommodated inside the scope 3.

The visible light reflection film 27 (an example of the reflection film) is provided between the oblique face 21a of the first prism 21 and the oblique face 22a of the second prism 22. In the present embodiment, the first prism 21 and the second prism 22 are fixed to each other via an adhesive after the visible light reflection film 27 is formed on any one of the oblique face 21a and the oblique face 22a. The visible light reflection film 27 is configured to separate the visible light and the near-infrared light from the biological tissue. More specifically, the visible light reflection film 27 is configured to reflect, toward the first trimming filter 23, the visible light emitted from the biological tissue and transmitted through the lens unit 20 and the first prism 21. Further, the visible light reflection film 27 is configured to transmit, toward the second trimming filter 25, the near-infrared light emitted from the biological tissue and transmitted through the lens unit 20 and the first prism 21.

Since the oblique face 21a of the first prism 21 and the oblique face 22a of the second prism 22 are inclined at 45 degrees with respect to the Z-axis direction, the visible light reflection film 27 is also inclined at 45 degrees with respect to the Z-axis direction. Therefore, the visible light reflection film 27 reflects the visible light such that a propagation direction of the visible light changes by 90 degrees, and transmits the near-infrared light such that a propagation direction of the near-infrared light does not change. As described above, the propagation direction of the visible light is converted from the Z-axis direction to the Y-axis direction by the visible light reflection film 27, while the propagation direction of the near-infrared light traveling in the Z-axis direction is not changed by the visible light reflection film 27.

The visible light reflection film 27 is a dichroic mirror made of a dielectric multilayer film formed by alternately laminating a dielectric thin film (high refractive index layer) having a high refractive index and a dielectric thin film (low refractive index layer) having a low refractive index. As a material of the high refractive index layer, for example, $TiO_2$ (refractive index $n_H=2.35$) may be used. As a material of the low refractive index layer, for example, $SiO_2$ (refractive index $n_L=1.47$) may be used. The number of high refractive index layers and the number of low refractive index layers are both, for example, 80.

Figure 3:
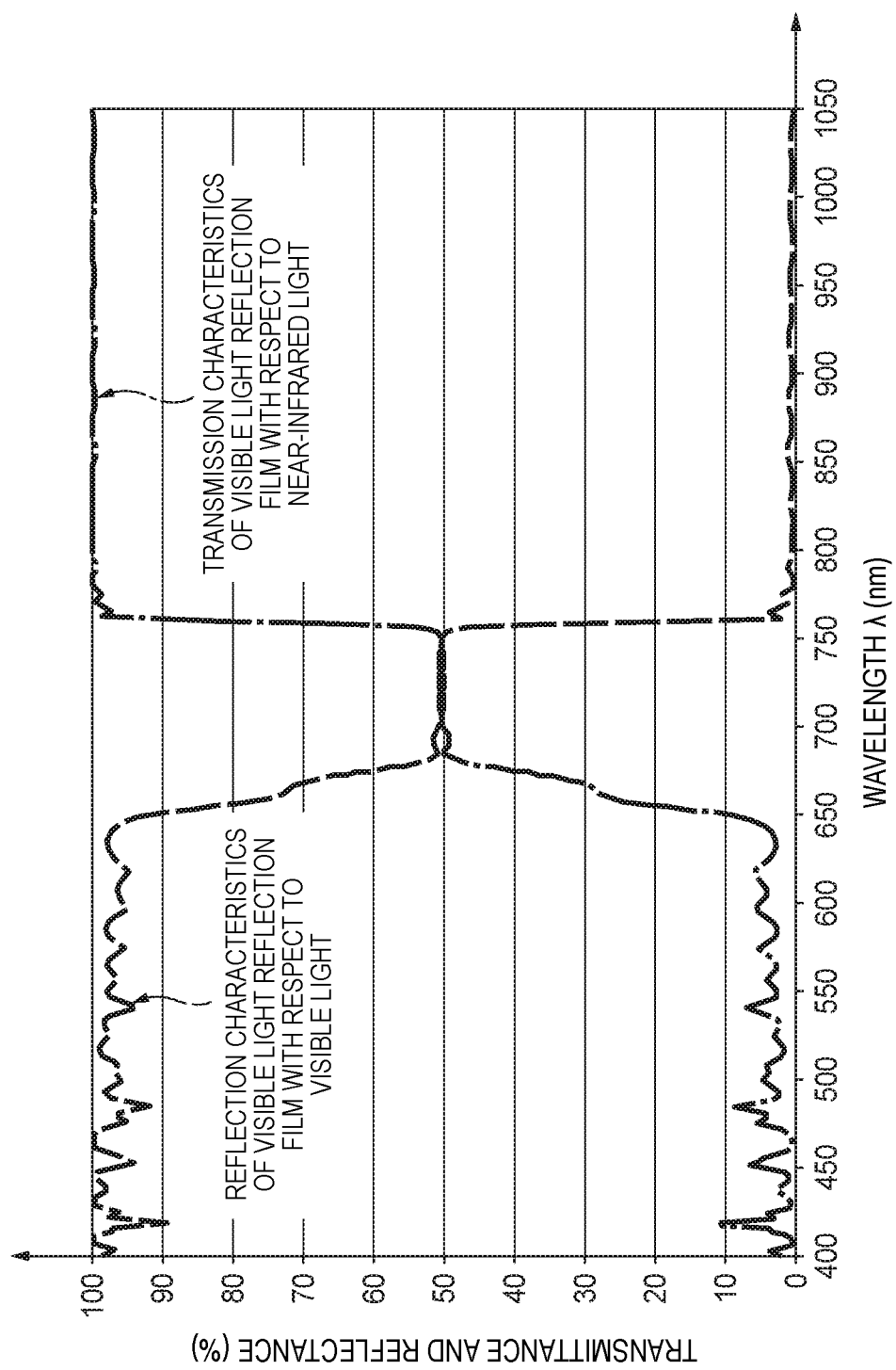
FIG. 3 is a diagram showing an example of reflection characteristics of a visible light reflection film with respect to visible light and transmission characteristics of the visible light reflection film with respect to near-infrared light.

FIG. 3 shows an example of reflection characteristics of the visible light reflection film 27 with respect to the visible light and transmission characteristics of the visible light reflection film 27 with respect to the near-infrared light. As shown in FIG. 3, the visible light reflection film 27 reflects the visible light such that reflectance with respect to visible light in a wavelength band of 400 nm to 650 nm is 90% or more. On the other hand, the visible light reflection film 27 hardly reflects near-infrared light in a wavelength band of 800 nm to 1050 nm. In other words, the visible light reflection film 27 transmits the visible light such that transmittance with respect to the visible light in the wavelength band of 400 nm to 650 nm is 10% or less. Further, the visible light reflection film 27 transmits most of the near-infrared light in the wavelength band of 800 nm to 1050 nm.

Figure 4:
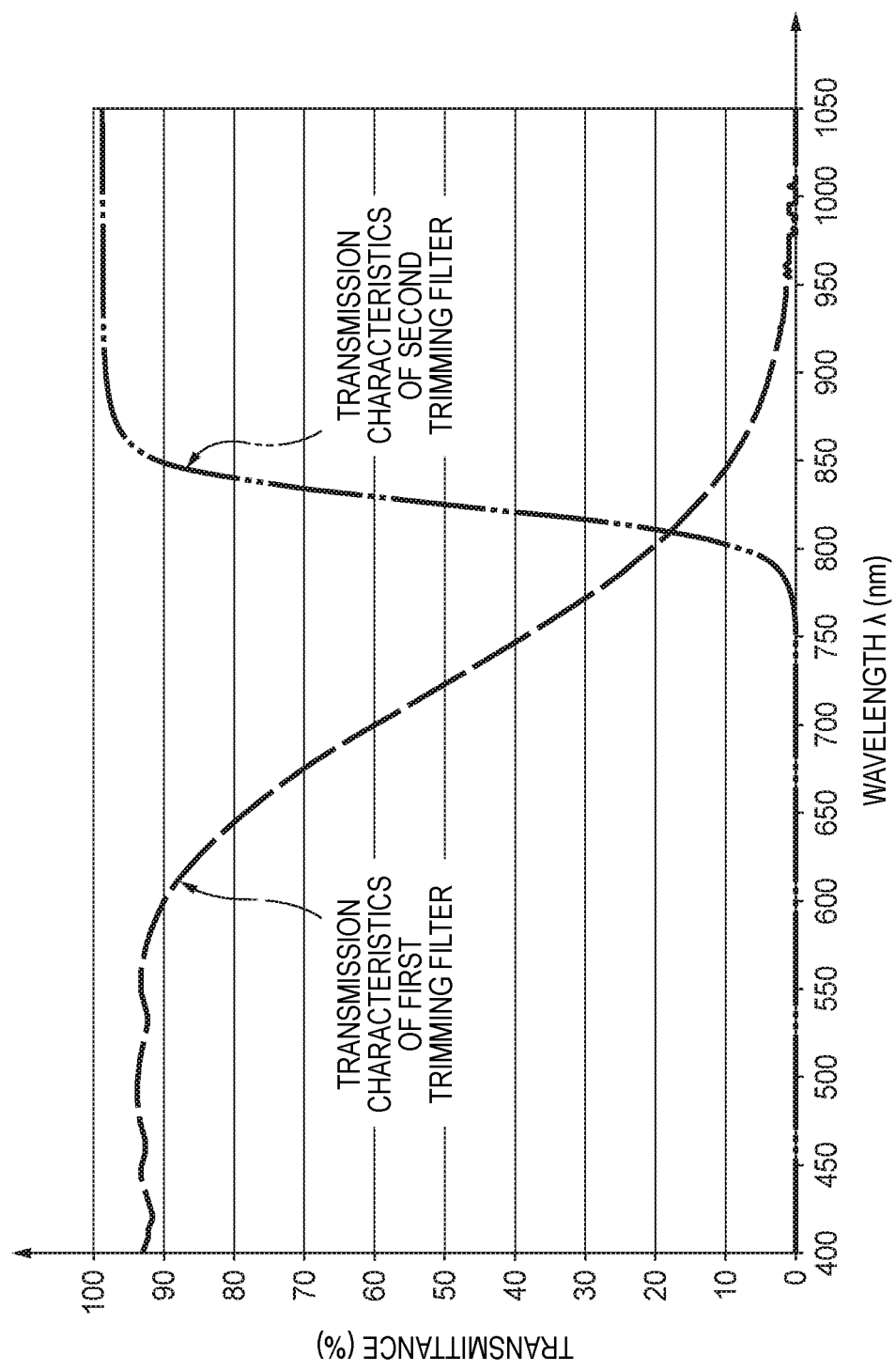
FIG. 4 is a diagram showing an example of transmission characteristics of a first trimming filter and transmission characteristics of a second trimming filter.

The first trimming filter 23 is fixed to the first prism 21 by an adhesive. An incident surface 23b of the first trimming filter 23 and an emission surface 21c of the first prism 21 are in contact with each other via an adhesive. The first trimming filter 23 is configured to transmit light (visible light) in a visible region and to shield light (near-infrared light) in a near-infrared region. The light reflected by the visible light reflection film 27 and transmitted through the first prism 21 is incident on the first trimming filter 23. The first trimming filter 23 transmits a visible light component in the incident light incident on the first trimming filter 23, and shields a near-infrared light component in the incident light. FIG. 4 shows an example of transmission characteristics of the first trimming filter 23. As shown in FIG. 4, transmittance of the first trimming filter 23 with respect to visible light in a wavelength band of 400 nm to 600 nm is 90% or more, while transmittance of the first trimming filter 23 with respect to near-infrared light in a wavelength of 800 nm or more is 20% or less. The first trimming filter 23 is formed of color glass that shields infrared light.

Figure 5:
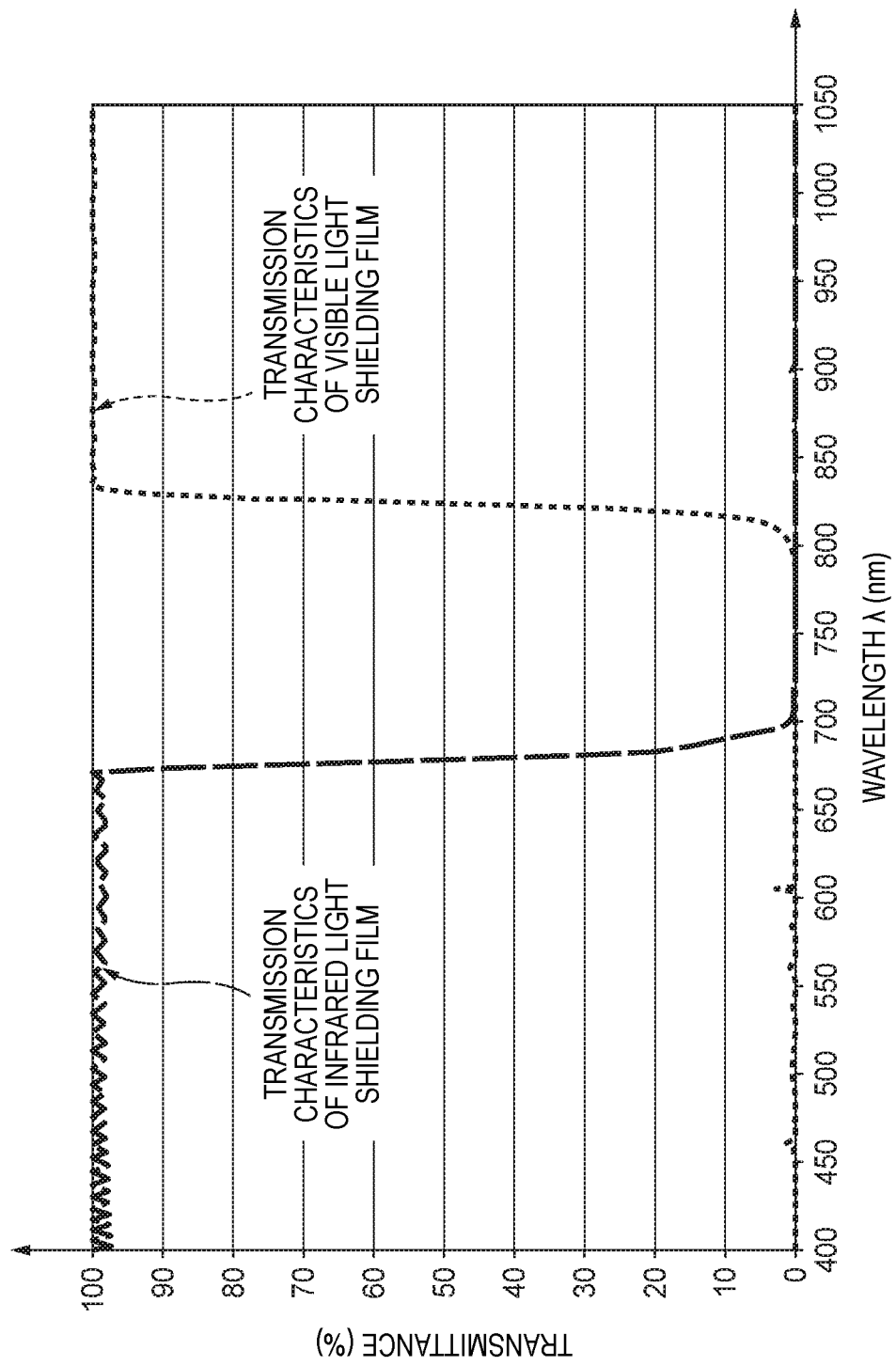
FIG. 5 is a diagram showing an example of transmission characteristics of an infrared light shielding film and transmission characteristics of a visible light shielding film.

The infrared light shielding film 28 is provided between the first trimming filter 23 and the first image sensor 24 in the Y-axis direction. In the present embodiment, the first trimming filter 23 and the first image sensor 24 are fixed to each other via an adhesive after the infrared light shielding film 28 is formed on an emission surface 23a of the first trimming filter 23. The infrared light shielding film 28 is configured to transmit light (visible light) in the visible region and to shield light (near-infrared light) in the near-infrared region and the excitation light emitted to the biological tissue and included in a wavelength band having a center wavelength of 700 nm to 800 nm. The infrared light shielding film 28 transmits a visible light component in the incident light transmitted through the first trimming filter 23 and incident on the infrared light shielding film 28, and shields a near-infrared light component in the incident light. FIG. 5 shows an example of transmission characteristics of the infrared light shielding film 28. As shown in FIG. 5, transmittance of the infrared light shielding film 28 with respect to visible light in a wavelength band of 400 nm to 650 nm is 95% or more, while transmittance with respect to light having a wavelength of 700 nm or more is 1% or less.

The infrared light shielding film 28 is a dichroic mirror made of a dielectric multilayer film formed by alternately laminating a high refractive index layer and a low refractive index layer. As a material of the high refractive index layer, for example, $TiO_2$ (refractive index $n_H=2.35$) may be used. As a material of the low refractive index layer, for example, $SiO_2$ (refractive index $n_L=1.47$) may be used. The number of high refractive index layers and the number of low refractive index layers are both, for example, 50.

Figure 6:
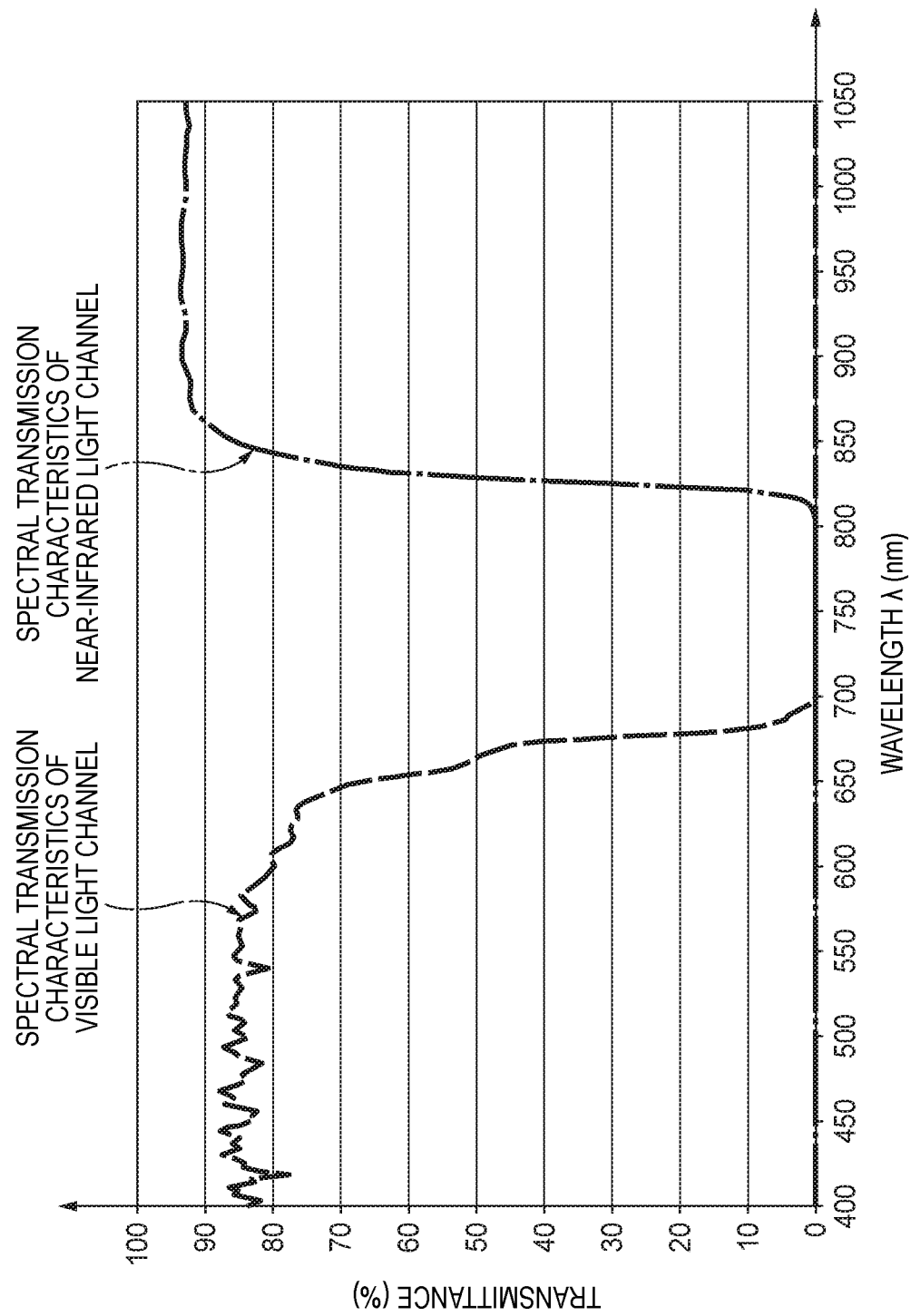
FIG. 6 is a diagram showing an example of spectral transmission characteristics of a visible light channel and spectral transmission characteristics of a near-infrared light channel.

Thus, the visible light reflected by the biological tissue of the patient is incident on the first image sensor 24 through a visible light channel formed by a combination of the visible light reflection film 27, the first trimming filter 23, and the infrared light shielding film 28. FIG. 6 shows an example of spectral transmission characteristics of the visible light channel formed by the combination of the visible light reflection film 27, the first trimming filter 23, and the infrared light shielding film 28. As shown in FIG. 6, transmittance of the visible light channel with respect to visible light in a wavelength band of 400 nm to 600 nm is 80% or more, and transmittance of light in a wavelength band of 720 nm to 1050 nm is 0.1% or less. In this regard, the visible light channel preferably has spectral characteristics such that transmittance of the light in the wavelength band of 720 nm to 1050 nm is 0.01% or less.

The first image sensor 24 is mounted on the first circuit board 32, and is disposed such that an imaging surface thereof faces the first trimming filter 23 and the infrared light shielding film 28 in the Y-axis direction. The first image sensor 24 is fixed to the first trimming filter 23 by an adhesive with the infrared light shielding film 28 interposed therebetween. The first image sensor 24 is configured to receive visible light transmitted through the visible light channel formed by the combination of the visible light reflection film 27, the first trimming filter 23, and the infrared light shielding film 28, and to convert the received visible light into an electric signal.

The first image sensor 24 is a complementary metal oxide semiconductor (CMOS) image sensor or a couple charged device (CCD) image sensor. In this regard, since the visible light incident on the image capturing unit 2 is incident on the first image sensor 24 after being reflected once by the visible light reflection film 27, an image of the biological tissue incident on the first image sensor 24 is an inverted image. On the other hand, the first image sensor 24 is preferably a CMOS image sensor because the CMOS image sensor can generate a visible light image signal indicating a normal image of the biological tissue based on the visible light forming the inverted image of the biological tissue. In this regard, by adjusting the order in which charges accumulated in photodiodes of the CMOS image sensor are read, a visible light image signal indicating the normal image of the biological tissue can be generated.

Figure 8:
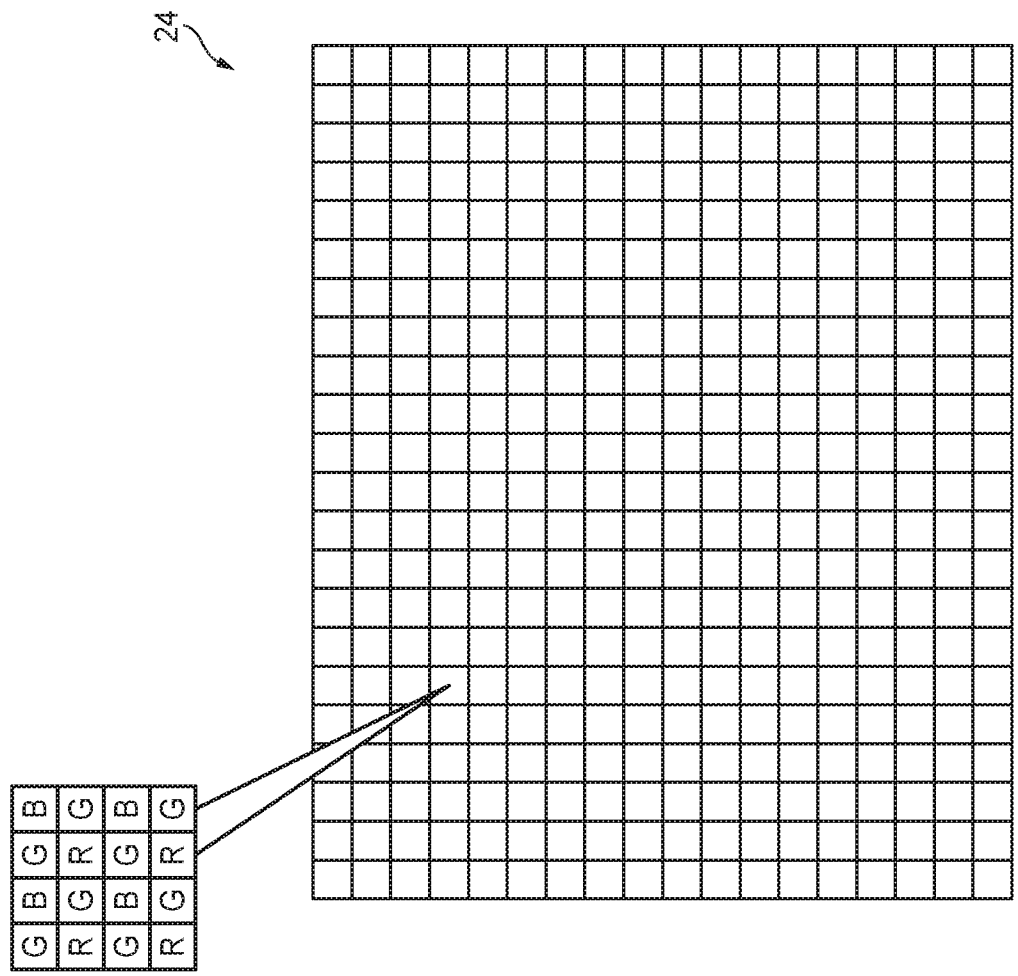
FIG. 8 is a diagram schematically showing a CMOS image sensor including Bayer pattern RGB color filters.

As shown in FIG. 8, the first image sensor 24 includes a Bayer pattern color filter array and a photodiode array having a plurality of photodiodes arranged in a matrix. The color filter array includes a plurality of red filters, a plurality of green filters, and a plurality of blue filters. In the Bayer pattern color filter array, the number of green filters is twice the number of red filters and the number of blue filters. Each photodiode included in the photodiode array faces one of the plurality of color filters (the red filter, the green filter, and the blue filter). Thus, the first image sensor 24 converts the received visible light into an electric signal to generate a visible light image signal (RAW data) indicating an image of the biological tissue, and then transmits the generated visible light image signal to a visible light image data generation circuit 41 (see FIG. 9) via an electric wiring 35. Thereafter, the visible light image data generation circuit 41 generates visible light image data by performing image data conversion processing (RAW data→RGB data) on the visible light image signal (RAW data). In the following description, the red filter, the green filter, and the blue filter of the color filter array may be collectively referred to simply as "RGB color filters".

Figure 7:
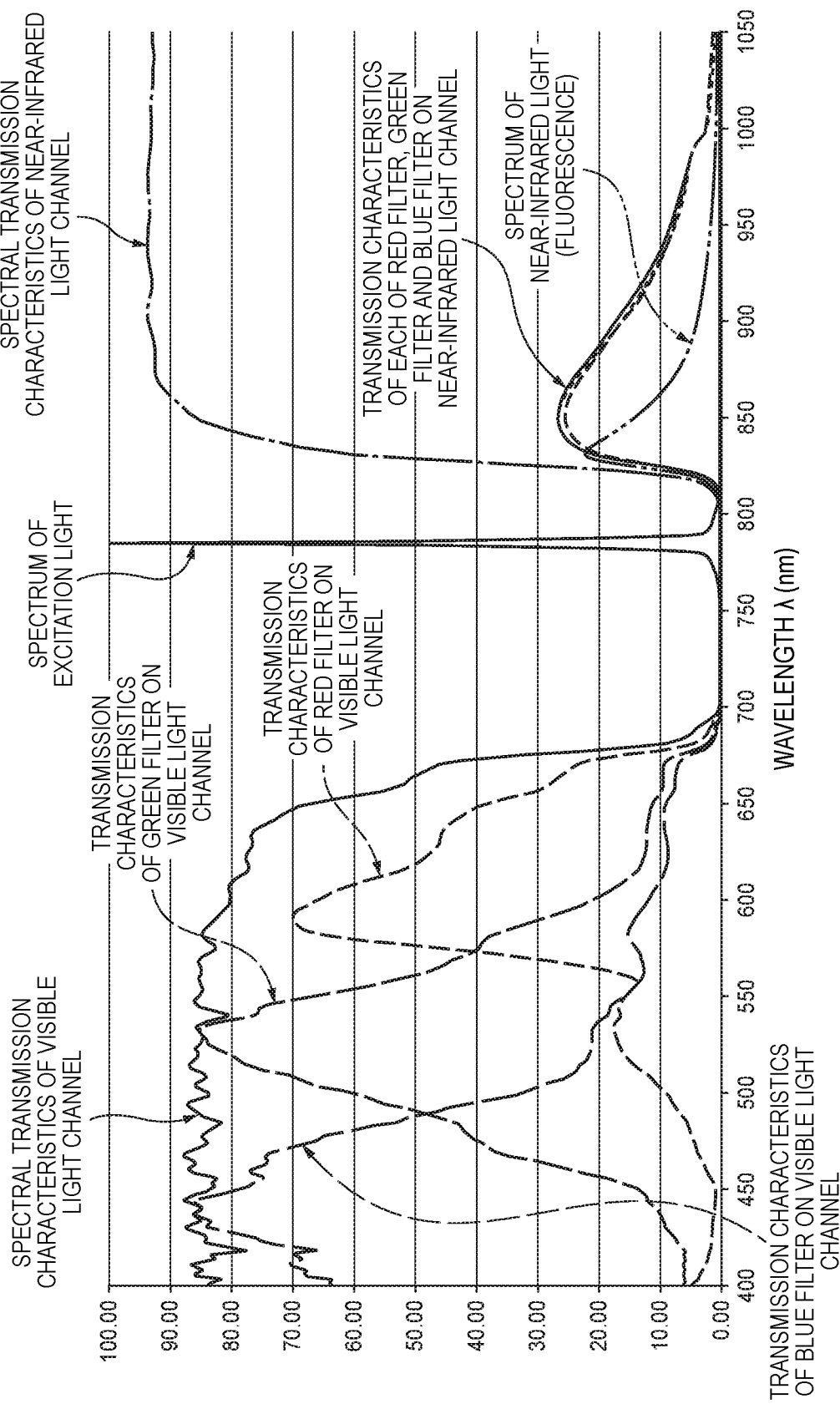
FIG. 7 is a diagram illustrating transmission characteristics of an RGB color filter on the visible light channel and transmission characteristics of an RGB color filter on the near-infrared light channel.

FIG. 7 shows transmission characteristics of the RGB color filters on the visible light channel. The visible light from the biological tissue passes through the visible light channel of the image capturing unit 2, and then passes through the RGB color filters of the first image sensor 24. Thereafter, the visible light passing through the RGB color filters is received by the photodiodes. As shown in FIG. 7, regarding transmission characteristics of the red filter on the visible light channel, transmittance of light in a wavelength of 720 nm or more is 0.1% or less. Regarding transmission characteristics of the green filter on the visible light channel, transmittance of light in a wavelength of 720 nm or more is 0.1% or less. Regarding transmission characteristics of the blue filter on the visible light channel, transmittance of light in a wavelength of 720 nm or more is 0.1% or less.

In this way, the excitation light having a center wavelength of 700 nm to 800 nm (more specifically, the excitation laser light having a center wavelength of 785 nm to 795 nm) and emitted to the biological tissue and the near-infrared light is suitably prevented from passing through the RGB color filters. As a result, the excitation light and the near-infrared light is suitably prevented from being received by the photodiodes of the first image sensor 24, accuracy or reliability of the visible light image data indicating the biological tissue is improved.

The second trimming filter 25 is fixed to the second prism 22 by an adhesive. An incident surface 25b of the second trimming filter 25 and an emission surface 22b of the second prism 22 are in contact with each other via an adhesive. The second trimming filter 25 is configured to transmit light (near-infrared light) in the near-infrared region and to shield light (visible light) in the visible region. The light transmitted through the visible light reflection film 27 and the second prism 22 is incident on the second trimming filter 25. The second trimming filter 25 transmits a near-infrared light component in the incident light incident on the second trimming filter 25, and shields a visible light component in the incident light. FIG. 4 shows an example of transmission characteristics of the second trimming filter 25. As shown in FIG. 4, transmittance of the second trimming filter 25 with respect to near-infrared light having a wavelength of 850 nm or more is 90% or more, while transmittance of the second trimming filter 25 with respect to visible light in a wavelength band of 400 nm to 750 nm is 1% or less. The second trimming filter 25 is formed of color glass that shields visible light.

The visible light shielding film 29 is provided between the second trimming filter 25 and the second image sensor 26 in the Z-axis direction. In the present embodiment, the second trimming filter 25 and the second image sensor 26 are fixed to each other via an adhesive after the visible light shielding film 29 is formed on the emission surface 25a of the second trimming filter 25. The visible light shielding film 29 is configured to transmit the light (near-infrared light) in the near-infrared region and to shield the light (visible light) in the visible region and the excitation light emitted to the biological tissue and included in a wavelength band having a center wavelength of 700 nm to 800 nm. The visible light shielding film 29 transmits a near-infrared light component in the incident light transmitted through the second trimming filter 25 and incident on the visible light shielding film 29, and shields a visible light component in the incident light. FIG. 5 shows an example of transmission characteristics of the visible light shielding film 29. As shown in FIG. 5, transmittance of the visible light shielding film 29 with respect to near-infrared light having a wavelength of 850 nm or more is 95% or more, while transmittance of the visible light shielding film 29 with respect to light in a wavelength band of 700 nm to 800 nm is 1% or less.

The visible light shielding film 29 is a dichroic mirror made of a dielectric multilayer film formed by alternately laminating a high refractive index layer and a low refractive index layer. As a material of the high refractive index layer, for example, $TiO_2$ (refractive index $n_H$=2.35) may be used. As a material of the low refractive index layer, for example, $SiO_2$ (refractive index $n_L$=1.47) may be used. The number of high refractive index layers and the number of low refractive index layers are both, for example, 50.

Thus, the near-infrared light emitted from the fluorescent contrast agent existing in the biological tissue is incident on the second image sensor 26 through a near-infrared light channel formed by a combination of the visible light reflection film 27, the second trimming filter 25, and the visible light shielding film 29. FIG. 6 shows an example of spectral transmission characteristics of the near-infrared light channel formed by the combination of the visible light reflection film 27, the second trimming filter 25, and the visible light shielding film 29. As shown in FIG. 6, transmittance of the near-infrared light channel with respect to near-infrared light having a wavelength of 870 nm or more is 90% or more, and transmittance of the near-infrared light channel with respect to light in a wavelength band of 400 nm to 798 nm is 0.5% or less. In this regard, the near-infrared light channel preferably has spectral characteristics such that transmittance of the light in the wavelength band of 400 nm to 798 nm is 0.01% or less.

The second image sensor 26 is mounted on the second circuit board 33, and is disposed such that an imaging surface thereof faces the second trimming filter 25 and the visible light shielding film 29 in the Z-axis direction. The second image sensor 26 is fixed to the second trimming filter 25 by an adhesive with the visible light shielding film 29 interposed therebetween. The imaging surface of the second image sensor 26 and the imaging surface of the first image sensor 24 are perpendicular to each other. The second image sensor 26 is configured to receive near-infrared light transmitted through the near-infrared light channel formed by the combination of the visible light reflection film 27, the second trimming filter 25, and the visible light shielding film 29, and to convert the received near-infrared light into an electric signal.

The second image sensor 26 converts the received near-infrared light into an electric signal to generate a near-infrared light image signal indicating an image of the biological tissue, and then transmits the generated near-infrared light image signal to a near-infrared light image data generation circuit 42 (see FIG. 9) via an electric wiring 36. Thereafter, the near-infrared light image data generation circuit 42 generates near-infrared light image data by performing predetermined processing on the near-infrared light image signal.

The second image sensor 26 is a CMOS image sensor or a CCD image sensor. In this regard, the second image sensor 26 and the first image sensor 24 preferably have the same configuration from a viewpoint of manufacturing cost of the endoscope 1. In this case, there is no need to prepare different types of image sensors for the first image sensor 24 and the second image sensor 26, the manufacturing cost of the endoscope 1 can be reduced. For example, similarly to the first image sensor 24, the second image sensor 26 may include a Bayer pattern color filter array and a photodiode array having a plurality of photodiodes arranged in a matrix. In the following description, it is assumed that the second image sensor 26 includes a Bayer pattern color filter array.

FIG. 7 shows transmission characteristics of the RGB color filters on the near-infrared light channel. The near-infrared light emitted from the fluorescent contrast agent existing on the biological tissue passes through the near-infrared light channel of the image capturing unit 2, and then passes through the RGB color filters of the second image sensor 26. Thereafter, the near-infrared light passing through the RGB color filters is received by the photodiodes. As shown in FIG. 7, regarding transmission characteristics of the blue filter on the near-infrared light channel, transmittance of light in a wavelength band of 400 nm to 798 nm is 0.5% or less, while transmittance of light in a vicinity of a wavelength of 850 nm is the highest. Similarly, regarding transmission characteristics of the green filter on the near-infrared light channel, transmittance of light in a wavelength band of 400 nm to 798 nm is 0.5% or less, while transmittance of light in a vicinity of a wavelength of 850 nm is the highest. Similarly, regarding transmission characteristics of the red filter on the near-infrared light channel, transmittance of light in a wavelength band of 400 nm to 798 nm is 0.5% or less, while transmittance of light in a vicinity of a wavelength of 850 nm is the highest. Further, as shown in FIG. 7, according to spectral characteristics of fluorescence (near-infrared light) output from the fluorescent contrast agent, a central wavelength of the near-infrared light exists in a vicinity of a wavelength of 830 nm.

Thus, even if the second image sensor 26 includes the Bayer pattern color filter array, the near-infrared light output from the fluorescence contrast agent can be converted into an electric signal, and the visible light and the excitation light is suitably prevented from being received by the photodiodes of the second image sensor 26. Therefore, the manufacturing cost of the endoscope 1 is reduced, and accuracy or reliability of the near-infrared light image data indicating the biological tissue is improved.

Further, in the single image sensor disclosed in JP-A-2016-209143, there are four types of pixels including a blue pixel, a green pixel, a red pixel, and an IR pixel. Therefore, there is a problem that a pixel value of the IR pixel is low, noise is likely to occur in an near-infrared light image signal output from a single IR pixel of the image sensor, and image quality of the near-infrared light image data may be deteriorated. Meanwhile, in the second image sensor 26, since all the pixels are IR pixels, a pixel value of each IR pixel can be increased through H/V pixel addition processing which is processing of adding pixel values of pixels adjacent in a horizontal (H) direction and a vertical (V) direction. In this way, in the second image sensor 26, the pixel value of each IR pixel is increased through the H/V pixel addition processing, so that the noise is less likely to occur in the near-infrared light image signal output from the second image sensor 26, and the accuracy or reliability of the near-infrared light image data indicating the biological tissue is improved.

Figure 9:
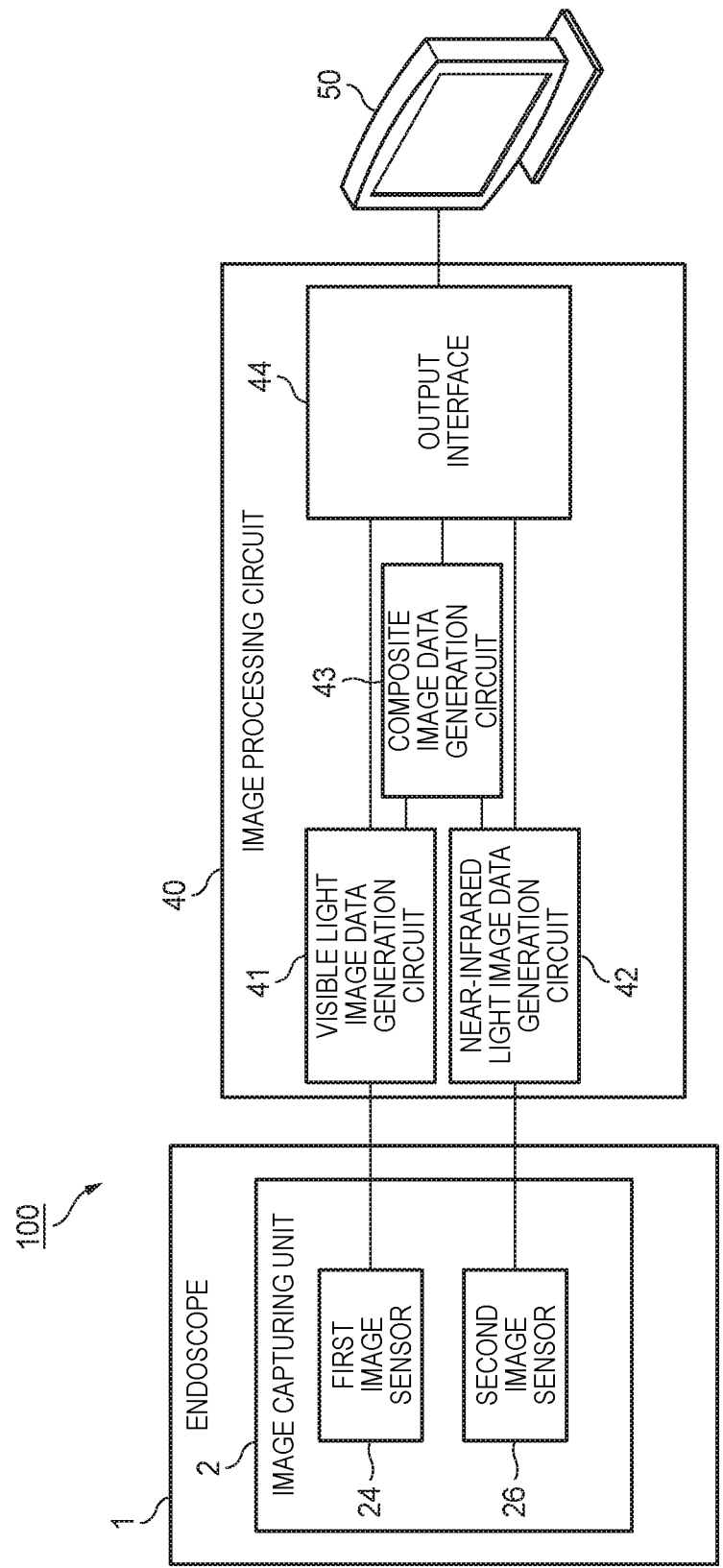
FIG. 9 is a diagram illustrating a configuration of an endoscope system.

Next, an endoscope system 100 will be described below with reference to FIG. 9. FIG. 9 is a diagram illustrating a configuration of the endoscope system 100. As shown in FIG. 9, the endoscope system 100 includes the endoscope 1 including the image capturing unit 2, an image processing circuit 40, and a display unit 50. In FIG. 9, for convenience of description, only a part of configurations of the endoscope 1 and the image processing circuit 40 are shown. The image processing circuit 40 includes the visible light image data generation circuit 41, the near-infrared light image data generation circuit 42, a composite image data generation circuit 43, and an output interface 44.

The image processing circuit 40 is configured to generate image data indicating the biological tissue based on an image signal (digital signal) transmitted from the image capturing unit 2 and then transmit the generated image data to the display unit 50. The image processing circuit 40 generates image data at a predetermined frame rate (for example, 60 fps). The frame rate of the image data is not particularly limited. In the present embodiment, the image processing circuit 40 can generate the visible light image data and the near-infrared light image data at the same timing and the same frame rate.

The image processing circuit 40 may include a microcomputer including one or more processors and one or more memories, and an electronic circuit including a passive element and an active element such as a transistor. The processor is, for example, at least one of a central processing unit (CPU), a micro processing unit (MPU), and a graphics processing unit (GPU). The memory includes a read only memory (ROM) and a random access memory (RAM). In addition to or instead of the microcomputer, the image processing circuit 40 may be a non-von Neumann computer such as an application specific integrated circuit (ASIC) or a field-programmable gate array (FPGA).

As described above, the visible light image data generation circuit 41 is configured to receive the visible light image signal (RAW data) from the first image sensor 24 and then generate the visible light image data based on the visible light image signal. The visible light image data generation circuit 41 transmits the visible light image data to the composite image data generation circuit 43 and the output interface 44.

The near-infrared light image data generation circuit 42 is configured to receive the near-infrared light image signal from the second image sensor 26 and then generate the near-infrared light image data based on the near-infrared light image signal. The near-infrared light image data generation circuit 42 transmits the near-infrared light image data to the composite image data generation circuit 43 and the output interface 44.

Figure 10:
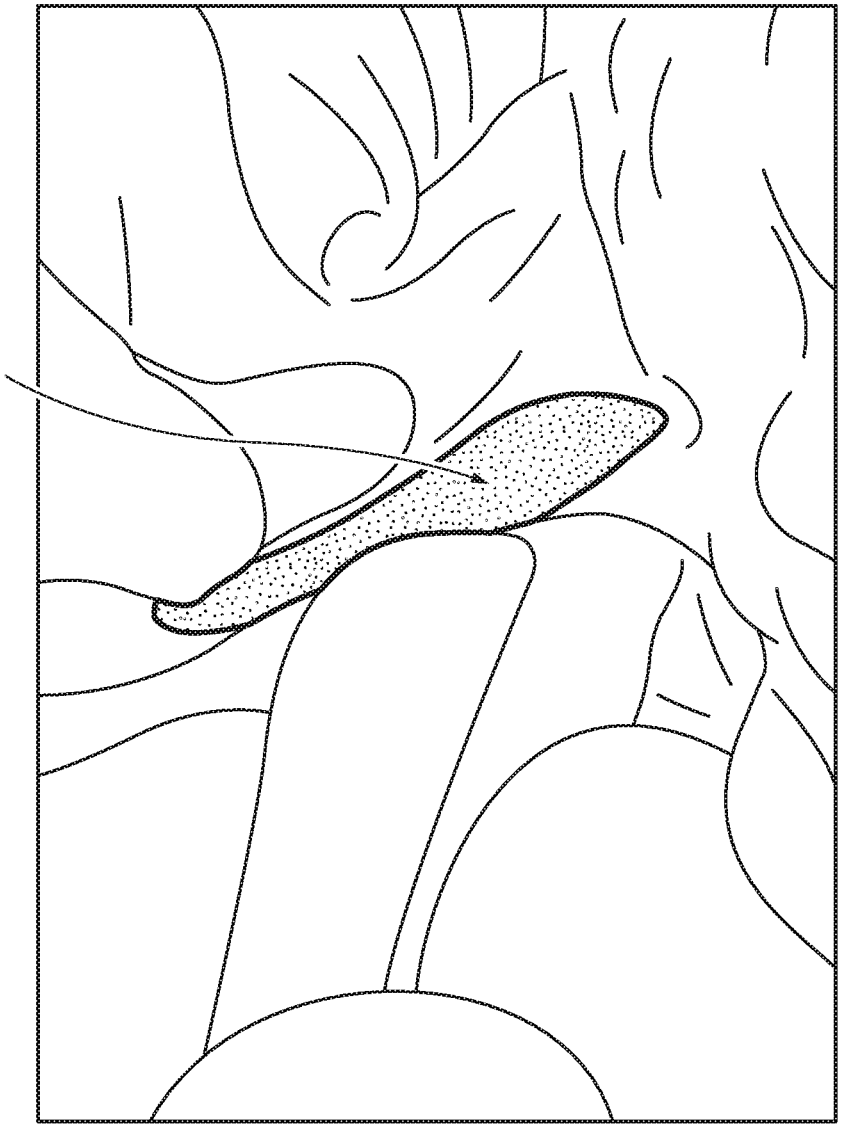
FIG. 10 is a diagram showing an example of composite image data obtained by synthesizing visible light image data and near-infrared light image data.

The composite image data generation circuit 43 is configured to generate composite image data by synthesizing the received visible light image data and near-infrared light image data. The composite image data generation circuit 43 may generate the composite image data after coloring the near-infrared light image data with a predetermined color (fluorescent color). Since the near-infrared light image data shows the biological tissue in which the fluorescent contrast agent such as ICG exists, when the near-infrared light image data is colored with a predetermined color, the biological tissue (affected part) in which the fluorescent contrast agent exists is highlighted and displayed on the composite image data (see, for example, FIG. 10). Therefore, a health care worker such as a surgeon can clearly grasp the affected part by visually recognizing the composite image data displayed on the display unit 50.

The visible light image data, the near-infrared light image data, and the composite image data are transmitted to the display unit 50 through the output interface 44. The display unit 50 is configured to display at least one of the visible light image data, the near-infrared light image data, and the composite image data. The image data transmitted to the display unit 50 may be appropriately changed according to an operation of the health care worker on the endoscope system 100. The display unit 50 may be a liquid crystal display or an organic EL display, or may be a transmissive or non-transmissive head-mounted display mounted on a head of a health care worker.

According to present embodiment, the first prism 21 and the second prism 22, which are right-angle prisms, are fixed to each other. The first trimming filter 23 is fixed to the first prism 21 and the first image sensor 24, and the second trimming filter 25 is fixed to the second prism 22 and the second image sensor 26. Further, the imaging surface of the first image sensor 24 and the imaging surface of the second image sensor 26 are perpendicular to each other. With such a configuration, the size of the entire image capturing unit 2 can be reduced, and the image capturing unit 2 can be accommodated inside the space S of the scope 3 having a small inner diameter. Since the image capturing unit 2 is accommodated inside the space S in the vicinity of the tip end surface 1a of the endoscope 1, the visible light and the near-infrared light associated with the biological tissue of the patient is efficiently received by the first image sensor 24 and the second image sensor 26, respectively. In this way, since the visible light image signal indicating the biological tissue is acquired by the first image sensor 24 without lowering a SN ratio (signal-to-noise ratio), the image quality of the visible light image data indicating the biological tissue is improved. Further, since the near-infrared light image signal indicating the biological tissue is acquired by the second image sensor 26, the image quality of the near-infrared light image data indicating the biological tissue is improved. Since the visible light image signal and the near-infrared light image signal are acquired at the same timing, a time axis of each frame of the visible light image data and a time axis of each frame of the near-infrared light image data match with each other. Thus, since the time axis of the frame of the visible light image data and the time axis of the frame of the near-infrared light image data match, accuracy of the composite image data generated by synthesizing the visible light image data and the near-infrared light image data is improved. Further, since the image capturing unit 2 is accommodated inside the space S of the scope 3, there is no need to provide, on the scope 3, an expensive relay lens or the like for guiding the visible light and the near-infrared light from the biological tissue of the patient to the image capturing unit 2, so that the manufacturing cost of the entire endoscope 1 can be reduced. Therefore, it is possible to provide the endoscope 1 capable of improving the image quality of the visible light image data, the near-infrared light image data, and the composite image data indicating the biological tissue of the patient while reducing the manufacturing cost.

According to the present embodiment, in a case where the first image sensor 24 is a COMS image sensor configured to generate the visible light image signal indicating the normal image of the biological tissue, the visible light image data and the near-infrared light image data can be acquired at the same timing. Specifically, in a case where the first image sensor 24 is a CCD image sensor, it is necessary to separately perform, on an image processing circuit 40 side, image inversion processing for generating the visible light image data indicating the normal image of the biological tissue based on the visible light image signal indicating the inverted image of the biological tissue. For this reason, a situation may occur in which the generation timing of the visible light image data is later than the generation timing of the near-infrared light image data, and it is difficult to acquire the visible light image data and the near-infrared light image data at the same timing on the image processing circuit 40 side. Meanwhile, in a case where the first image sensor 24 is a CMOS image sensor, since there is no need to perform the image inversion processing on the image processing circuit 40 side, the visible light image data and the near-infrared light image data can be acquired at the same timing on the image processing circuit side.

According to the present embodiment, the visible light channel formed by the combination of the visible light reflection film 27, the first trimming filter 23, and the infrared light shielding film 28 has spectral characteristics such that transmittance of light in a wavelength band of 720 nm to 1050 nm is 0.1% or less. Therefore, a situation in which the excitation light in a wavelength band of 700 nm to 800 nm and the near-infrared light both being emitted to the biological tissue adversely affect the accuracy or reliability of the visible light image data can be suitably prevented. Further, the near-infrared light channel formed by the combination of the visible light reflection film 27, the second trimming filter 25, and the visible light shielding film 29 has spectral characteristics such that transmittance of light in a wavelength band of 400 nm to 798 nm is 0.5% or less. Therefore, a situation in which the excitation light and the visible light emitted to the biological tissue adversely affects the accuracy or reliability of the near-infrared light image data can be suitably prevented. Further, in the second image sensor 26, the pixel value of each IR pixel is increased through the H/V pixel addition processing, so that the noise is less likely to occur in the near-infrared light image signal output from the second image sensor 26, and the accuracy or reliability of the near-infrared light image data is improved.

Although the embodiment of the present invention has been described above, it is needless to say that the technical scope of the present invention should not be interpreted as being limited to the description of the present embodiment. It is to be understood by those skilled in the art that the present embodiment is merely an example and various modifications of the embodiment may be made within the scope of the invention described in the claims. The technical scope of the present invention should be determined based on the scope of the invention described in the claims and the equivalent scope thereof.

In the present embodiment, the visible light reflection film 27 has been described as an example of a reflection film that separates the visible light and the near-infrared light from the biological tissue, but the reflection film is not limited to the visible light reflection film. For example, the reflection film that separates the visible light and the near-infrared light may be a near-infrared light reflecting film configured to transmit the visible light and reflect the near-infrared light. In this case, a position of the first prism 21 and a position of the second prism 22 are interchanged with each other, and a position of the first trimming filter 23 on which the infrared light shielding film 28 is formed and a position of the second trimming filter 25 on which the visible light shielding film 29 is formed are interchanged with each other. Further, a position of the first image sensor 24 and a position of the second image sensor 26 are interchanged with each other. Similarly, the near-infrared light reflection film is also a dichroic mirror made of a dielectric multilayer film formed by alternately laminating a dielectric thin film (high refractive index layer) having a high refractive index and a dielectric thin film (low refractive index layer) having a low refractive index.

In the present embodiment, the first prism 21 and the second prism 22 are configured as right-angle prisms, but a shape of the first prism 21 or the second prism 22 is not limited to a right-angled triangular prism.

The first image sensor 24 and the second image sensor 26 may have configurations different from each other. For example, the second image sensor 26 may not include the color filter array. In this case, since the near-infrared light channel disposed in front of the second image sensor 26 shields the visible light and the excitation light while transmitting the near-infrared light, only the near-infrared light can be incident on the photodiodes of the second image sensor 26.

The invention claimed is:

1. An endoscope comprising:
   a scope to be inserted into a body of a patient; and
   an image capturing assembly accommodated inside the scope and configured to receive light associated with biological tissue of the patient so as to capture an image of the biological tissue,
   wherein the image capturing assembly comprises:
      a first prism;
      a second prism facing the first prism;
      a reflection film provided between an oblique face of the first prism and an oblique face of the second prism and configured to separate the light associated with the biological tissue into visible light and near-infrared light;
      a first trimming filter configured to transmit light in a visible region and to shield light in a near-infrared region, the visible light transmitted through the first prism being incident on the first trimming filter via the reflection film;
      a first image sensor facing the first trimming filter so as to receive the visible light transmitted through the first trimming filter, and configured to convert the received visible light into an electric signal;
      a second trimming filter configured to transmit light in the near-infrared region and to shield light in the visible region, the near-infrared light transmitted through the second prism being incident on the second trimming filter via the reflection film;
      a second image sensor facing the second trimming filter so as to receive the near-infrared light transmitted through the second trimming filter, and configured to convert the received near-infrared light into an electric signal;
      an infrared light shielding film provided between the first trimming filter and the first image sensor and configured to transmit light in the visible region and to shield light in the near-infrared region; and
      a lens assembly fixed to the first prism so as to guide the light associated with the biological tissue toward the first prism,
   wherein the first prism is fixed to the second prism,
   wherein the first trimming filter is fixed to the first prism,
   wherein the second trimming filter is fixed to the second prism,
   wherein the first image sensor is fixed to the first trimming filter,
   wherein the second image sensor is fixed to the second trimming filter, and
   wherein the imaging capturing assembly is located inside a distal end part of the scope.

2. The endoscope according to claim 1,
   wherein the image capturing assembly is disposed in a vicinity of a tip end surface of the endoscope facing the biological tissue.

3. The endoscope according to claim 1,
   wherein the image capturing assembly further comprises:
      a visible light shielding film provided between the second trimming filter and the second image sensor and configured to transmit light in the near-infrared region and to shield light in the visible region, and
   wherein the infrared light shielding film and the visible light shielding film are configured to shield excitation light emitted to the biological tissue and included in a wavelength band having a center wavelength of 700 nm to 800 nm.

4. The endoscope according to claim 1,
   wherein a distance between a tip end of the lens assembly and a tip end surface of the endoscope facing the biological tissue is in a range of 0.5 mm to 5 mm.

5. The endoscope according to claim 1, further comprising:
   a first support member configured to support the lens assembly, the first prism, and the second prism, and accommodated inside the scope,
   wherein the first support member is fixed to the lens assembly, the first prism, and the second prism.

6. The endoscope according to claim 5 further comprising:
   a second support member fixed to the first support member and the scope and accommodated inside the scope.

7. The endoscope according to claim 1,
   wherein the first image sensor comprises a CMOS image sensor configured to generate, based on the visible light forming an inverted image of the biological tissue, a visible light image signal indicating a normal image of the biological tissue.

8. The endoscope according to claim 1, wherein the first image sensor and the second image sensor have a same configuration.

9. The endoscope according to claim 1, wherein an imaging surface of the first image sensor and an imaging surface of the second image sensor are perpendicular to each other.

10. The endoscope according to claim 3, wherein a visible light channel formed by a combination of the reflection film, the first trimming filter, and the infrared light shielding film has spectral characteristics such that transmittance of light in a wavelength band of 720 nm to 1050 nm is 0.1% or less, and
wherein a near-infrared light channel formed by a combination of the reflection film, the second trimming filter, and the visible light shielding film has spectral characteristics such that transmittance of light in a wavelength band of 400 nm to 798 nm is 0.5% or less.

11. The endoscope according to claim 1, wherein the scope is a part of the endoscope to be inserted into the body of the patient,
wherein the first trimming filter is adhered to the first prism,
wherein the second trimming filter is adhered to the second prism,
wherein the first image sensor is adhered to the first trimming filter, and
wherein the second image sensor is adhered to the second trimming filter.

12. An image capturing assembly accommodated inside a scope of an endoscope and configured to receive light associated with biological tissue of a patient so as to capture an image of the biological tissue, the image capturing assembly comprising:
a first prism;
a second prism facing the first prism;
a reflection film provided between an oblique face of the first prism and an oblique face of the second prism and configured to separate the light associated with biological tissue into visible light and near-infrared light;
a first trimming filter configured to transmit light in a visible region and to shield light in a near-infrared region, the visible light transmitted through the first prism being incident on the first trimming filter via the reflection film;
a first image sensor facing the first trimming filter so as to receive the visible light transmitted through the first trimming filter, and configured to convert the received visible light into an electric signal;
a second trimming filter configured to transmit light in the near-infrared region and to shield light in the visible region, the near-infrared light transmitted through the second prism being incident on the second trimming filter via the reflection film;
a second image sensor facing the second trimming filter so as to receive the near-infrared light transmitted through the second trimming filter, and configured to convert the received near-infrared light into an electric signal;
an infrared light shielding film provided between the first trimming filter and the first image sensor and configured to transmit light in the visible region and to shield light in the near-infrared region; and a lens assembly fixed to the first prism so as to guide the light associated with the biological tissue toward the first prism,
wherein the first prism is fixed to the second prism,
wherein the first trimming filter is fixed to the first prism,
wherein the second trimming filter is fixed to the second prism,
wherein the first image sensor is fixed to the first trimming filter,
wherein the second image sensor is fixed to the second trimming filter, and
wherein the imaging capturing assembly is located inside a distal end part of the scope.

13. The endoscope according to claim 1, wherein the image capturing assembly is arranged such that a near-infrared light channel formed by the reflection film and the second trimming filter extends along an axial direction of the scope.

14. An endoscope comprising:
a scope to be inserted into a body of a patient; and
an image capturing assembly accommodated inside the scope and configured to receive light associated with biological tissue of the patient so as to capture an image of the biological tissue,
wherein the image capturing assembly comprises:
a first prism;
a second prism facing the first prism;
a reflection film provided between an oblique face of the first prism and an oblique face of the second prism and configured to separate the light associated with the biological tissue into visible light and near-infrared light;
a first trimming filter configured to transmit light in a visible region and to shield light in a near-infrared region, the visible light transmitted through the first prism being incident on the first trimming filter via the reflection film;
a first image sensor facing the first trimming filter so as to receive the visible light transmitted through the first trimming filter, and configured to convert the received visible light into an electric signal;
a second trimming filter configured to transmit light in the near-infrared region and to shield light in the visible region, the near-infrared light transmitted through the second prism being incident on the second trimming filter via the reflection film;
a second image sensor facing the second trimming filter so as to receive the near-infrared light transmitted through the second trimming filter, and configured to convert the received near-infrared light into an electric signal; and
an infrared light shielding film provided between the first trimming filter and the first image sensor and configured to transmit light in the visible region and to shield light in the near-infrared region,
wherein the first prism is fixed to the second prism,
the first trimming filter is fixed to the first prism,
wherein the second trimming filter is fixed to the second prism,
wherein the image capturing assembly further comprises a visible light shielding film provided between the second trimming filter and the second image sensor and configured to transmit light in the near-infrared region and to shield light in the visible region, and
wherein the infrared light shielding film and the visible light shielding film are configured to shield excitation light emitted to the biological tissue and included in a wavelength band having a center wavelength of 700 nm to 800 nm.

15. The endoscope according to claim 14, wherein a visible light channel formed by a combination of the reflection film, the first trimming filter, and the infrared light shielding film has spectral characteristics such that transmittance of light in a wavelength band of 720 nm to 1050 nm is 0.1% or less, and wherein a near-infrared light channel formed by a combination of the reflection film, the second trimming filter, and the visible light shielding film has spectral characteristics such that transmittance of light in a wavelength band of 400 nm to 798 nm is 0.5% or less.

\* \* \* \* \*